(12) United States Patent
Park et al.

(10) Patent No.: US 9,905,721 B2
(45) Date of Patent: Feb. 27, 2018

(54) LEAK DETECTING SENSOR AND CHEMICAL LIQUID INJECTION SYSTEM

(75) Inventors: Young-Kwang Park, Tokyo (JP); Takanobu Yagi, Tokyo (JP); Seiichi Ono, Tokyo (JP); Tomoyuki Kawabe, Tokyo (JP); Tatsuya Ito, Yokohama (JP)

(73) Assignee: NEMOTO KYORINDO CO., LTD., Tokyo (JP)

( * ) Notice: Subject to any disclaimer, the term of this patent is extended or adjusted under 35 U.S.C. 154(b) by 0 days.

(21) Appl. No.: 13/453,108

(22) Filed: Apr. 23, 2012

(65) Prior Publication Data

US 2013/0109967 A1     May 2, 2013

Related U.S. Application Data

(63) Continuation of application No. PCT/JP2012/058725, filed on Mar. 30, 2012.

(30) Foreign Application Priority Data

Mar. 31, 2011    (JP) ................................. 2011-078737

(51) Int. Cl.
*H01L 31/16*     (2006.01)
*A61M 5/00*     (2006.01)
(Continued)

(52) U.S. Cl.
CPC ............ *H01L 31/16* (2013.01); *A61B 5/0059* (2013.01); *A61M 5/007* (2013.01);
(Continued)

(58) Field of Classification Search
CPC ...... A61B 5/05; H01L 31/16; A61M 2205/15; A61M 2205/3306; A61M 5/14546; A61M 5/16831; A61M 5/007
(Continued)

(56) References Cited

U.S. PATENT DOCUMENTS 4,880,304 A    11/1989   Jaeb et al.
6,487,428 B1    11/2002   Culver et al.
(Continued)

FOREIGN PATENT DOCUMENTS

JP     A-1976-140673     12/1976
JP     U S54-053889      9/1977
(Continued)

OTHER PUBLICATIONS

Extended European Search Report in European Patent Application No. 12765349.1, dated Nov. 19, 2014.
(Continued)

*Primary Examiner* — Peter Luong
(74) *Attorney, Agent, or Firm* — Knobbe Martens Olson & Bear LLP

(57) ABSTRACT

To provide a leak detecting sensor capable of favorably detecting a leak of a chemical liquid regardless of orientation in fixing to a patient. The leak detecting sensor has a plurality of light-emitting elements 11 each emitting light to be applied to the patient, and a single light-receiving element receiving the light emitted by the plurality of light-emitting elements and reflected by the patient. The plurality of light-emitting elements are placed to surround the single light-receiving element.

11 Claims, 12 Drawing Sheets

(51) Int. Cl.
*A61B 5/00* (2006.01)
*A61M 5/145* (2006.01)
*A61M 5/168* (2006.01)
*A61B 1/04* (2006.01)

(52) U.S. Cl.
CPC .... *A61M 5/14546* (2013.01); *A61M 5/16831* (2013.01); *A61B 1/043* (2013.01); *A61M 2205/15* (2013.01); *A61M 2205/3306* (2013.01)

(58) Field of Classification Search
USPC .................................................. 600/473–478
See application file for complete search history.

(56) References Cited

U.S. PATENT DOCUMENTS

| | | | |
|---|---|---|---|
| 7,722,562 | B2 | 5/2010 | Hanlon et al. |
| 7,809,430 | B2 | 10/2010 | Ono et al. |
| 7,826,890 | B1 | 11/2010 | Winchester, Jr. et al. |
| 7,970,457 | B2 | 6/2011 | Ono et al. |
| 2004/0225255 | A1* | 11/2004 | Ono .......................... 604/65 |
| 2004/0254478 | A1* | 12/2004 | de Josselin de Jong et al. ........................ 600/476 |
| 2011/0021909 | A1 | 1/2011 | Ono et al. |
| 2012/0203080 | A1 | 8/2012 | Kim et al. |

FOREIGN PATENT DOCUMENTS

| | | |
|---|---|---|
| JP | A-1988246138 | 9/1988 |
| JP | Y H4-050009 | 11/1992 |
| JP | A H7-299042 | 11/1995 |
| JP | A-2000-237195 | 12/1999 |
| JP | A-2005-532841 | 11/2005 |
| JP | A-2006-68491 | 3/2006 |
| JP | A-2008-168111 | 7/2008 |
| JP | A-2008-212258 | 9/2008 |
| WO | WO 2001/08729 A1 | 2/2001 |
| WO | WO 2003/063680 A2 | 8/2003 |
| WO | WO 2006/030764 A1 | 3/2006 |
| WO | WO 2010/058796 | 5/2010 |
| WO | WO 2011/062356 A1 | 5/2011 |

OTHER PUBLICATIONS

Office Action in Japanese Patent Application No. 2013-507825, dated Feb. 23, 2016.
Notice of Reason(s) for Rejection in Japanese Patent Application No. 2013-507825, dated Dec. 8, 2015.
Notification of Reasons for Refusal in Japanese application No. 2016-133812 , dated Jun. 6, 2017.

* cited by examiner

LEAK DETECTING SENSOR AND CHEMICAL LIQUID INJECTION SYSTEM

TECHNICAL FIELD

The present invention relates to a leak detecting sensor for detecting a chemical liquid which should be injected into a blood vessel of a patient but is actually leaked to the outside of the blood vessel during the injection of the chemical liquid into the blood vessel with an injection needle. The present invention also relates to a chemical liquid injection system having the leak detecting sensor and a chemical liquid injector.

BACKGROUND ART

Currently employed medical imaging diagnosis apparatuses include CT apparatuses, MRI apparatuses, PET apparatuses, angiography apparatuses and the like. In using the abovementioned apparatuses to obtain diagnostic images of a patient, a chemical liquid such as a contrast medium or physiological saline is often injected into the patient's body.

The injection of the chemical liquid into the patient is performed by connecting an injection needle to a syringe filled with the chemical liquid through an extension tube, inserting the injection needle into a blood vessel of the patient, and pushing a piston of the syringe manually or with a chemical liquid injector. In this case, the tip of the injection needle may come off the blood vessel for some reason. If the chemical liquid is injected with the injection needle coming off the blood vessel, an extravascular leak or extravasation occurs in which the chemical liquid is leaked to a peripheral area outside the blood vessel.

A leak detecting sensor is used for detecting the extravascular leak. A conventional known leak detecting sensor is an optical reflective sensor as disclosed in Patent Document 1. The leak detecting sensor of this type typically has a sensor head fixed to a body surface of a patient near the position where an injection needle is inserted. The sensor head has a structure in which a pair of a light-emitting element and a light-receiving element and a circuit substrate for these elements are put in a housing. The sensor is fixed to the patient during the injection of the chemical liquid, for example using an adhesive sheet, such that a lower surface of the housing is in intimate contact with the patient. The light-emitting element and the light-receiving element are placed side by side so that the light-emitting element within the housing in intimate contact with the body surface of the patient emits light, the emitted light is reflected in the body (under the skin) of the patient, and the reflected light is received by the light-receiving element. The surface of the housing in intimate contact with the patient has an opening portion for passing the emitted light and the reflected light in order to direct the emitted light from the light-emitting element within the housing to the patient and to guide the reflected light from the patient to the light-receiving element within the housing.

PRIOR ART REFERENCES

Patent Document

Patent Document 1: International Publication WO06/030764

DISCLOSURE OF THE INVENTION

Problems to be Solved by the Invention

In the abovementioned conventional leak detecting sensor, however, the pair of the light-emitting element and the light-receiving element are placed side by side, so that the light irradiation range of the light-emitting element is not coincident with the light reception range of the light-receiving element. Thus, even when a leak of a chemical liquid occurs at the same site, the site of the leak may be present within the light reception range but may not be irradiated with the light from the light-emitting element, or conversely, the site of the leak may be irradiated with the light but may be outside the light reception range depending on the orientation of the sensor head fixed to the patient, with the result that the leak may not be detected. In addition, if the sensor head is not fixed securely and the patient moves during the injection of the chemical liquid, part of the contact surface of the sensor head may be raised from the patient. If the sensor head is raised at a position closer to the light-receiving element, the light-receiving element receives external light which may prevent the correct results of leak detection from being provided.

In the conventional leak detecting sensor, the opening portion for the light incidence and exit is formed in the surface in intimate contact with the patient. Thus, a concave portion of the opening portion is present in the contact surface and causes several problems as described below.

Since the sensor head is repeatedly used and the chemical liquid for injection may adhere thereto, the sensor head needs cleaning for each use from a hygienic viewpoint. However, if the chemical liquid enters into the concave portion of the opening portion, it is not removed easily. In addition, when the sensor head is used with the chemical liquid left in the concave portion, the light may be scattered by the chemical liquid to reduce the detection sensitivity.

It is an object of the present invention to provide a leak detecting sensor capable of detecting a leak of a chemical liquid without depending on the orientation of a fixed sensor head. It is another object of the present invention to provide a leak detecting sensor capable of stably detecting a leak of a chemical liquid without being affected easily by external light even when a sensor head is raised. It is yet another object of the present invention to provide a leak detecting sensor capable of eliminating various problems associated with the structure of a surface of a sensor head in intimate contact with a patient.

Means for Solving the Problems

The present invention provides a leak detecting sensor detecting a leak of a chemical liquid, which should be injected into a blood vessel of a patient, to the outside of the blood vessel. The leak detecting sensor includes:

a plurality of light-emitting elements each emitting light to be applied to the patient; and a single light-receiving element receiving the light emitted by the plurality of light-emitting elements and reflected by the patient, wherein the plurality of light-emitting elements are placed to surround the single light-receiving element.

The present invention also provides a chemical liquid injection system including:

the leak detecting sensor according to the present invention; and a chemical liquid injector injecting a chemical liquid of interest in detection of a leak by the leak detecting sensor, wherein the chemical liquid injector controls operation of injection of the chemical liquid and operation of the leak detecting sensor.

In the present invention, the leak detecting sensor further includes a housing holding the light-emitting elements and the light-receiving element. The housing has a plurality of opening portions formed therein for passing the light, the opening portions being formed at positions opposite to the light-emitting elements and the light-receiving element. The housing can also have a contact surface brought into intimate contact with a body surface of the patient in use. In this case, the opening portion opposite to the light-receiving element is preferably formed at the center of the contact surface in order that the sensor may be less susceptible to external light. An upper surface of the housing opposite to the contact surface is formed in a domical shape, so that the housing is fixed more securely to the patient by an adhesive sheet covering the housing. A light-transmitting member transmitting the light emitted by the light-emitting element is fitted in the opening portion, and thus the contact surface is flat including a lower surface of the light-transmitting member. This can eliminate the various problems caused by the concave portion formed in the contact surface due to the opening portion.

Effects of the Invention

According to the present invention, since the plurality of light-emitting elements and the single light-receiving element are placed as described above, any leak of the chemical liquid can be favorably detected regardless of the orientation of the sensor fixed to the patient to improve the flexibility in fixing the sensor to the patient. Since the plurality of light-emitting elements are placed to surround the light-receiving element, the light-receiving element is less susceptible to external light to allow more stable detection.

When the leak detecting sensor has the housing holding the light-emitting elements and the light-receiving element, the light-transmitting member is fitted in the opening portion formed in the contact surface of the housing in intimate contact with the patient to provide the flat contact surface including the lower surface of the light-transmitting member. Thus, a foreign matter or the chemical liquid does not tend to stay on the contact surface, which can prevent a reduction in detection sensitivity due to the foreign matter or the chemical liquid. Even when any foreign matter or the chemical liquid adheres to the contact surface, the foreign matter or the chemical liquid can be removed easily. According to the configuration including the light-transmitting member fitted in the opening portion, the light-transmitting member is in intimate contact with the patient in the site in which the opening portion is formed, and a certain intimate contact state can be achieved between the housing and the patient, so that more stable detection results can be achieved.

MODES FOR CARRYING OUT THE INVENTION

Figure 1:
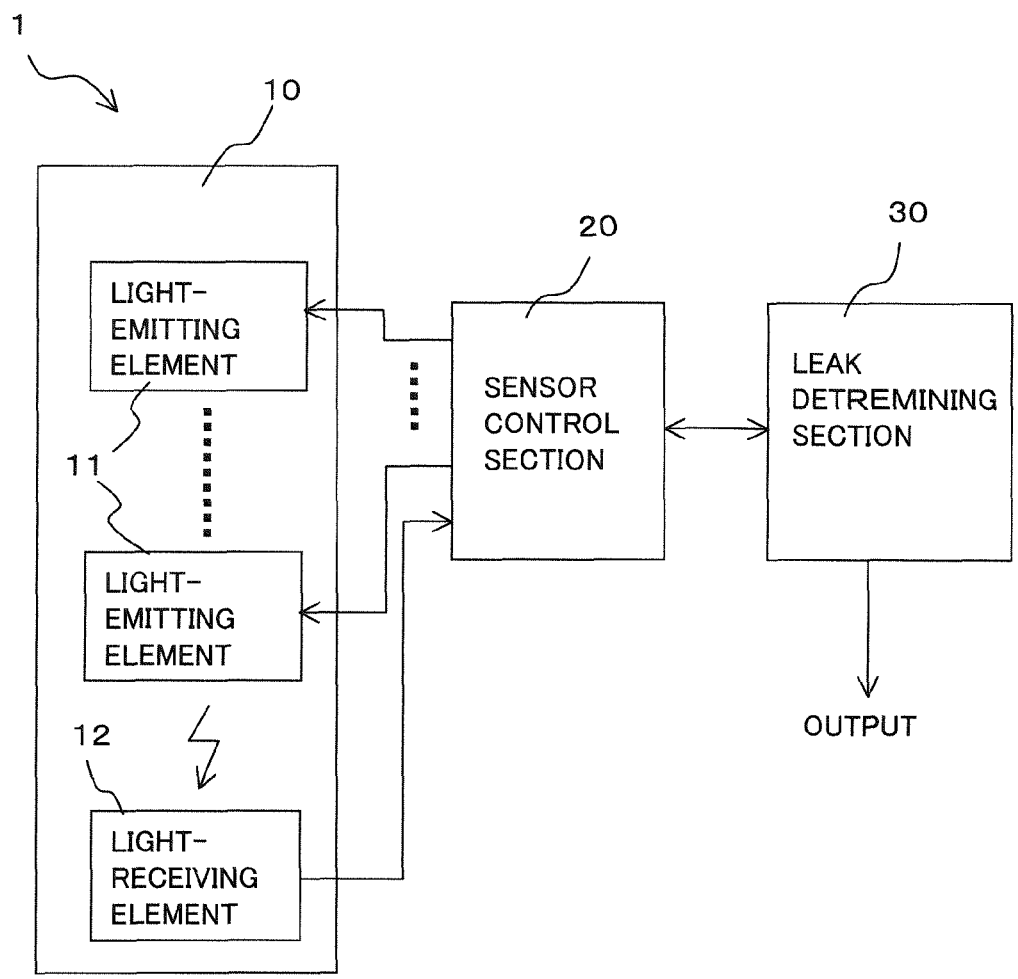
FIG. 1 A block diagram showing the configuration of a leak detecting sensor according to an embodiment of the present invention.

Referring to FIG. 1, a block diagram of leak detecting sensor 1 according to an embodiment of the present invention is shown which has sensor head 10, sensor control section 20, and leak determining section 30.

Sensor head 10 is fixed in intimate contact with a patient for use in injection of a chemical liquid and has a plurality of light-emitting elements 11 and one light-receiving element 12. Light-emitting element 11 is an element which emits light at a predetermined wavelength in response to application of a voltage. For example, a light-emitting diode which emits infrared rays can be used as light-emitting element 11. Light-receiving element 12 is an element which receives at least the light at the wavelength emitted by light-emitting element 11 to convert the light energy into electric energy, and the electric energy obtained through the conversion provides an electric output. For example, a phototransistor can be used as light-receiving element 12.

Sensor control section 20 is formed as a control circuit for the operation of light-emitting elements 11 and light-receiving element 12 and controls which light-emitting element 11 is driven in which timing in accordance with a preset procedure. Leak determining section 30 is an electric circuit which determines a leak of the chemical liquid based on a change in the electrical output value output from light-receiving element 12 and outputs a leak detection signal as an electric signal when it determines that the leak occurs.

Figure 2:
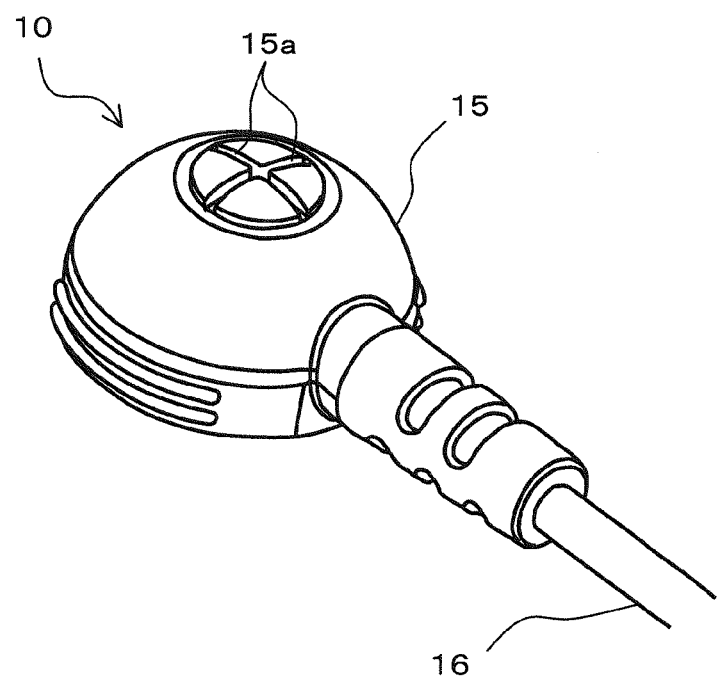
FIG. 2 A perspective view of an example of a sensor head shown in FIG. 1 viewed from above.
Figure 3:
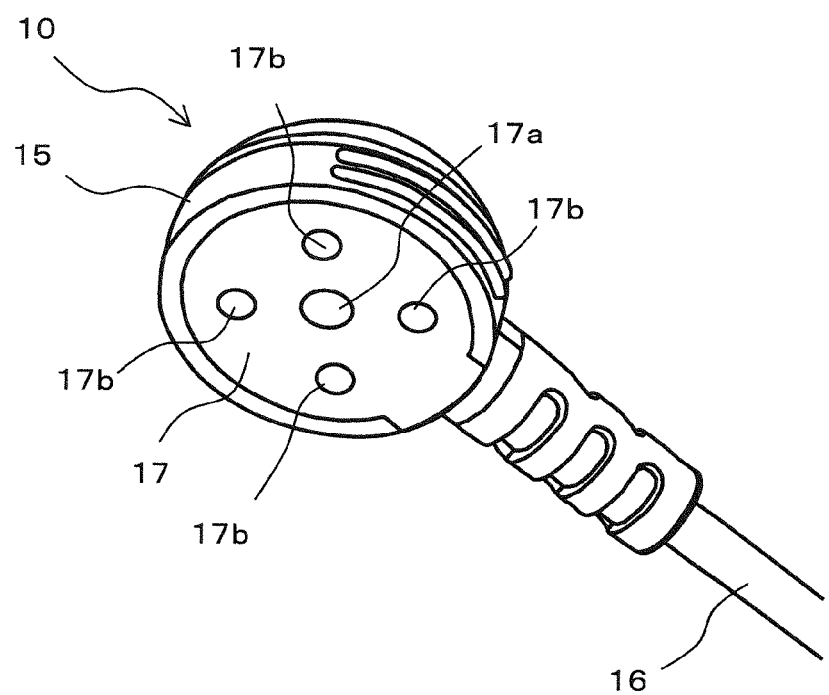
FIG. 3 A perspective view of the sensor head shown in FIG. 2 viewed from a contact surface in intimate contact with a patient.

As shown in FIG. 2 and FIG. 3, sensor head 10 is made of resin, for example, and has a shape in which contact surface 17 in intimate contact with a patient in use is generally circular and flat, and an upper surface opposite thereto is generally domical. Housing 15 is formed as a closed case and holds the plurality of light-emitting elements 11 and the one light-receiving element 12 therein. Two linear grooves 15a are formed to be orthogonal to each other as a cross groove at the center of an upper surface of housing 15.

Figure 4:
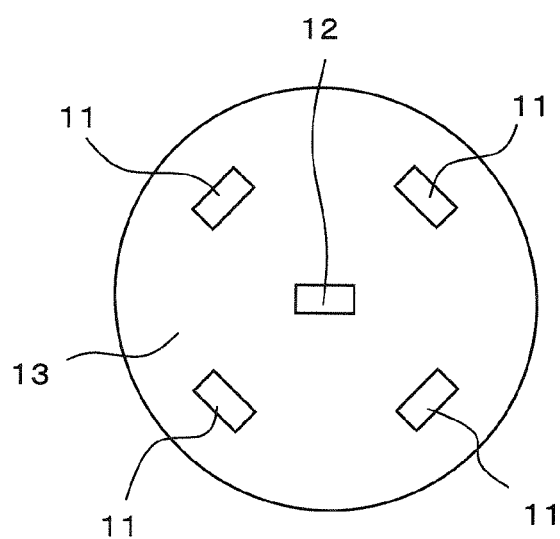
FIG. 4 A diagram showing an example of arrangement of light-emitting elements and a light-receiving element in the present invention.

Referring to FIG. 4, the present embodiment includes four light-emitting elements 11 and one light-receiving element 12. These light-emitting elements 11 and light-receiving element 12 are mounted on substrate 13 and fixed within housing 15. Light-receiving element 12 is mounted at a position corresponding to the center of contact surface 17 of housing 15, and four light-emitting elements 11 are mounted at positions surrounding light-receiving element 12 at equal distances from light-receiving element 12 and at equal angular intervals. This arrangement of light-emitting elements 11 and light-receiving element 12 causes the center of light emission regions of all light-emitting elements 11 to coincide with the center of a light reception region of light-receiving element 12. Since the present embodiment includes four light-emitting elements 11, these light-emitting elements 11 are placed at an interval of 90 degrees around light-emitting element 12.

Substrate 13 on which one light-receiving element 12 and four light-emitting elements 11 are placed as described above is fixed to housing 15 such that, for example, light-receiving element 12 is located at the intersection of two grooves 15a (see FIG. 2) and four light-emitting elements 11 are placed symmetrically with respect to two grooves 15a when viewed from contact surface 17.

Opening portion 17a at the center and four opening portions 17b around opening portion 17a are formed in contact surface 17 of housing 15.

Opening portion 17a is located at the center of contact surface 17 to be opposite to light-receiving element 12 placed within housing 15. Light-receiving element 12 receives light which enters into housing 15 through opening portion 17a. In this manner, the light entering into housing 15 through opening portion 17a is applied to light-receiving element 12. Thus, housing 15 is preferably formed not to pass external light therethrough. To this end, for example, housing 15 can be made of a material which does not pass external light therethrough, an inner surface of housing 15 can be colored black by painting or the like, or a combination thereof can be used.

Four opening portions 17b are formed at equal angular intervals around opening portion 17a to be opposite to associated light-emitting elements 11. Light from each of light-emitting elements 11 is emitted to the outside of housing 15 through opposite opening portion 17b.

The light irradiation range of light-emitting element 11 and the light reception range of light-receiving element 12 are influenced by the shapes of opening portions 17b and 17a, respectively. In view of the efficient use of the light emitted by light-emitting element 11, opening portions 17a and 17b preferably have circular shapes.

Figure 5:
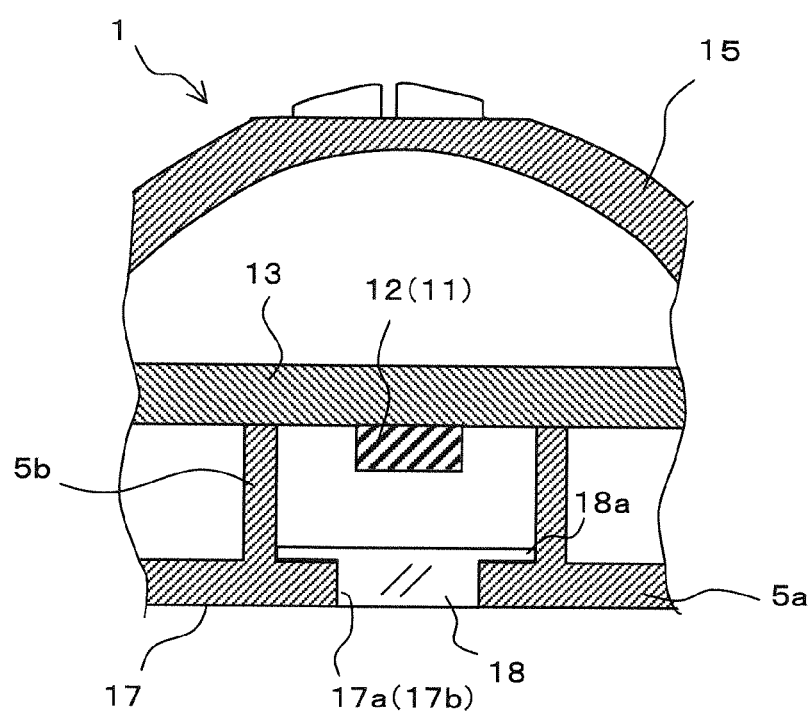
FIG. 5 A simplified longitudinal section view of the sensor head shown in FIG. 2 at the position including a light-receiving element.

FIG. 5 shows a longitudinal section view of main portions of sensor head 10 in the area in which opening portion 17a at the center is formed. As shown in FIG. 5, light-transmitting member 18 which passes the light emitted by light-emitting element 11 (not shown in FIG. 5) is fitted in opening portion 17a from inside housing 15. Light-transmitting member 18 has a cross section with a size and a shape identical to those of opening portion 17a so as not to produce a gap between light-transmitting member 18 and an inner circumferential surface of opening portion 17a.

Flange portion 18a is formed at one end of light-transmitting member 18 in a thickness direction. Light-transmitting member 18 is mounted with flange portion 18a located inside housing 15 and is held on an inner surface of housing 15 so as not to come off opening portion 17a by adhering flange portion 18a to the inner surface of housing 15. Flange portion 18a can be adhered by using an adhesive or an adhesive tape. Flange portion 18a included by light-transmitting member 18 structurally prevents easy entrance of a foreign matter or the chemical liquid into housing 15. The thickness of light-transmitting member 18 except flange portion 18a is equal to the thickness of a lower wall of housing 15, so that a lower surface of housing 15 is flush with a lower surface of light-transmitting member 18.

While the description has been made of the structure including opening portion 17a opposite to light-receiving element 12 in FIG. 5, opening portion 17b opposite to light-emitting element 11 is formed in the same manner such that light-transmitting member 18 is fitted and held in each of opening portions 17b from inside housing 15. Since light-transmitting member 18 is fitted in each of opening portions 17a and 17b, the overall lower surface of housing 15 forms flat contact surface 17 including the lower surfaces of light-transmitting members 18.

Figure 6:
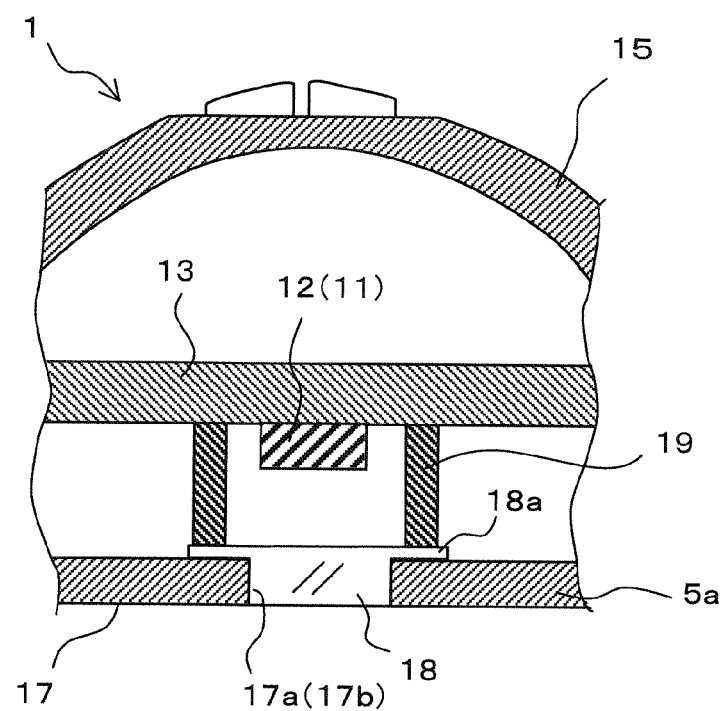
FIG. 6 A longitudinal section view showing a modification of a structure of holding a light-transmitting member in the sensor head shown in FIG. 2.

FIG. 5 shows light-transmitting member 18 held on the inner surface of housing 15 through the adhesion. Alternatively, as shown in FIG. 6, light-transmitting member 18 can be held on the inner surface of housing 15 by forming hold member 19 in housing 15 between lower wall 5a of housing 15 and substrate 13 to press flange portion 18a of light-transmitting member 18 against lower wall 5a from inside housing 15.

Since light-transmitting member 18 has flange portion 18a in this manner, flange portion 18a can be used to hold light-transmitting member 18 on housing 15 in various manners. The use of flange portion 18a to hold light-transmitting member 18 can reliably hold light-transmitting member 18 on housing 15 without any influence on the light passing through light-transmitting member 18.

As shown in FIG. 5, partition 5b is formed inside housing 15 to extend from lower wall 5a of housing 15 to substrate 13 to entirely surround opening portion 17a (each opening portion 17b) and light-receiving element 12 (each light-emitting element 11) opposite thereto. This can independently provide the path of the light emitting from each light-emitting element 11 to the outside of housing 15 through opening portion 17b and the path of the light reaching light-receiving element 12 from outside housing 15 through opening portion 17a, and as a result, the accuracy of leak detection can be improved. In the structure for holding light-transmitting member 18 shown in FIG. 6, hold member 19 can be formed to entirely surround opening portion 17a (opening portion 17b) and light-receiving element 12 (light-emitting element 11) in order for hold member 19 to achieve the same effects as those of partition 5b shown in FIG. 5.

Referring again to FIG. 2 and FIG. 3, cable 16 for transmitting an electric signal extends from housing 15. In the block diagram shown in FIG. 1, sensor control section 20 and leak determining section 30 are electrically connected to sensor head 10 through cable 16. Sensor control section 20 and leak determining section 30 may be formed as an integral and independent unit separate from sensor head 10, or may be incorporated into sensor head 10, or may be provided as one of functions of a chemical liquid injector which is used together with leak detecting sensor 1 to inject a patient with a chemical liquid of interest in detection of any leak by leak detecting sensor 1. When sensor control section 20 and leak determining section 30 are incorporated into sensor head 10, cable 16 can be used as a cable for power supply, for example. In addition, sensor control section 20 and leak determining section 30 may be formed as independent units, and one of them may be incorporated into sensor head 10, or may be provided as one of the functions of the chemical liquid injector, or may be provided independently of sensor head 10 and the chemical liquid injector. In the present invention, a combination of leak detecting sensor 1 and the chemical liquid injector is referred to as a chemical liquid injection system.

When sensor control section 20 and leak determining section 30 are formed as independent units, leak detecting sensor 1 can also include a display device and/or a sound output device in order to notify an operator of the determination result of leak determining section 30.

On the other hand, when sensor control section 20 and leak determining section 30 are formed as one of the functions of the chemical liquid injector, these sensor control section 20 and leak determining section 30 are incorporated into the chemical liquid injector, so that sensor head 10 is connected to the chemical liquid injector through cable 16. Cable 16 may be connected removably to the chemical liquid injector through an appropriate connector (not shown).

A power source (not shown) is connected to leak detecting sensor 1, and leak detecting sensor 1 operates on power supplied from the power source. The power source can be provided by using a DC power source which receives an AC power from a commercial power source and outputs a predetermined DC power, or a battery such as a dry battery, a secondary battery, and a fuel cell.

A dedicated power source is typically prepared for operating leak detecting sensor 1. When sensor control section 20 is incorporated in the chemical liquid injector, a power source for supplying power to the chemical liquid injector can be shared with the chemical liquid injector to supply power from the power source for the chemical liquid injector to sensor control section 20.

Leak determining section 30 is preferably connected to a control section of the chemical liquid injector such that the leak detection signal output from leak determining section 30 is input to the control section of the chemical liquid injector. This allows the control section of the chemical liquid injector to stop the injection operation of the chemical liquid based on the input leak detection signal to minimize the leak.

As described above, in the leak detecting sensor, all the functions can be contained in sensor head 10, some of the functions can be provided by the unit independent of sensor head 10, some of the functions can be incorporated and provided in the chemical liquid injector, or some of the functions can be provided by the unit independent of sensor head 10 and some of the remaining functions can be incorporated and provided in the chemical liquid injector. The connection between sensor head 10 and the unit provided independently of sensor head 10 (including the unit incorporated in the chemical liquid injector) can be achieved with wired connection through cable 16 described above or the like or wireless connection.

The chemical liquid injector is described with reference to FIG. 7 and FIG. 8.

Figure 7:
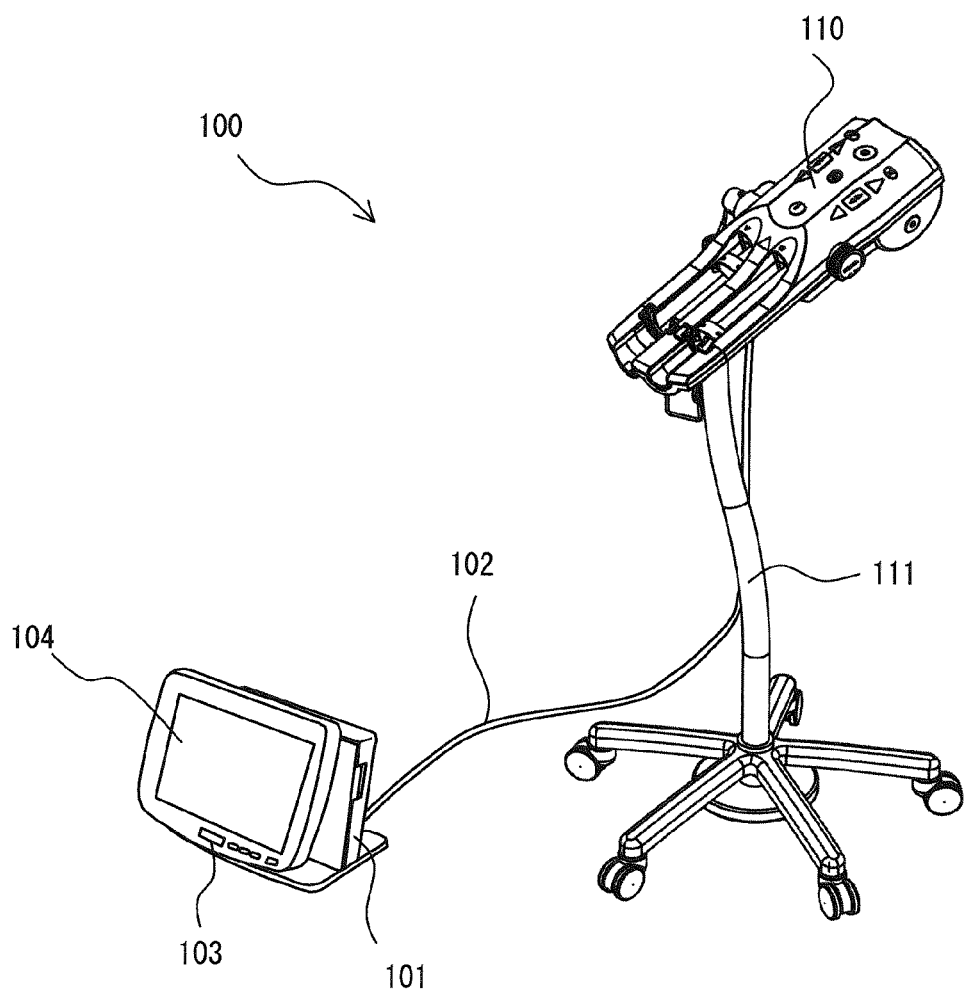
FIG. 7 A perspective view of a chemical liquid injector which is an example of an external apparatus used together with the leak detecting sensor according to the present invention.

For example as shown in FIG. 7, chemical liquid injector 100 has injection head 110 pivotally attached to the top of stand 111 and injection control unit 101 connected electrically to injection head 110 through cable 102. Injection control unit 101 has main operation panel 103 and touch panel 104 doubling as display means and input means. Injection control unit 101 may further include a hand-held unit (not shown) which is auxiliary input means connected electrically to a body of injection control unit 101 through a cable, not shown.

Injection control unit 101 includes a single computer unit including a CPU, a RAM, and a ROM which functions as a control section for controlling the overall operation of the chemical liquid injector. When sensor control section 20 and leak determining section 30 (see FIG. 1) of leak detecting sensor 1 are provided as one of the functions of chemical liquid injector 100, sensor control section 20 and leak determining section 30 can be configured within the computer unit. The determination result of leak determining section 30 can be displayed on touch panel 104.

Figure 8:
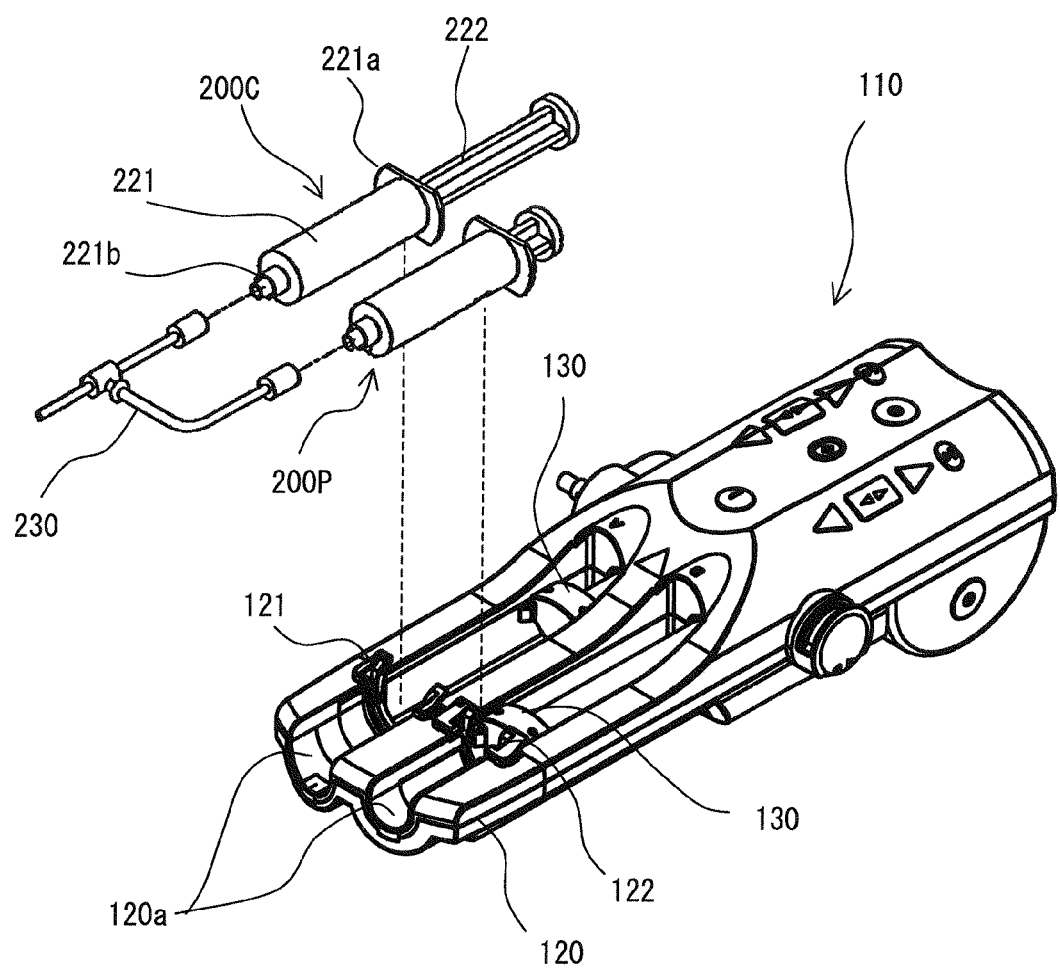
FIG. 8 A perspective view showing an injection head shown in FIG. 7 and a syringe to be mounted thereon.

As shown in FIG. 8, two syringes 200C and 200P are removably mounted side by side on injection head 110. Each of syringes 200C and 200P has cylinder 221 having cylinder flange 221a formed at a trailing end and nozzle portion 221b formed at a leading end and piston 222 inserted into cylinder 221 to be movable forward and backward.

When piston 222 is moved forward toward the leading end of cylinder 221, the chemical liquid filled therein is pushed from each of syringes 200C and 200P through nozzle portion 221b. Nozzle portions 221b of syringes 200C and 200P are connected to two trailing ends of extension tube 230 connected to an injection needle at a leading end and branched into two at some midpoint. Syringes 200C and 200P, extension tube 230 and the like constitute a syringe unit. The injection needle can be inserted into a blood vessel of a patient to inject the chemical liquid filled in syringes 200C and 200P into the patient. Examples of the chemical liquid filled in syringes 200C and 200P include a contrast medium and physiological saline. For example, one syringe 200C can be filled with the contrast medium, and the other syringe 200P can be filled with the physiological saline.

Syringe receiver 120 for placing two syringes 200C and 200P thereon is formed in a leading end portion on an upper surface of injection head 110. Syringe receiver 120 has two concave portions 120a each formed to receive an outer circumferential surface of cylinder 221. Syringe adapters 121 and 122 are removably mounted on syringe receiver 120 to hold cylinder flanges 221a of syringes 200C and 200P.

Syringes 200C and 200P mounted on syringe receiver 120 are fixedly mounted on injection head 110 by placing each cylinder 221 in concave portion 121 with nozzle portion 221b directed toward the leading end and holding cylinder flange 221a. However, syringes 200C and 200P vary in size and/or shape, and it is difficult to hold cylinder flanges 221a of all those types of syringes 200C and 200P on a common holding structure. Thus, in the present embodiment, a plurality of types of syringe adapters 121 and 122 having holding structures appropriate for respective holding cylinder flanges 221a and removably mounted on syringe receiver 120 are prepared for the respective shapes of syringes 200C and 200P to be mounted. Syringe adapters 121 and 121 can be exchanged depending on the types of syringes 200C and 200P to mount various sizes and/or syringes 200C and 200P on injection head 110.

In injection head 110, two piston driving mechanisms 130 driven independently for individually or simultaneously moving pistons 222 of mounted syringes 200C and 200P forward/backward are provided in association with the positions in which syringes 200C and 200P are mounted.

Piston driving mechanism 130 has a driving motor (not shown), a motion transformation mechanism (not shown) for transforming a rotation output of the driving motor into a linear motion, and a piston holding mechanism (not shown) connected to the motion transformation mechanism and holding a trailing end of piston 222 to be freely engaged or disengaged in order to move piston 222 forward and backward. Since such piston driving mechanism 130 can be provided by using a known mechanism typically used in the chemical liquid injector, detailed description thereof is omitted herein.

For injecting the chemical liquid with chemical liquid injector 100, injection head 110 is set in a treatment room where a patient stands by, and injection control unit 101 is often set in an operation room different from the treatment room. Thus, when sensor control section 20 and leak determining section 30 of leak detecting apparatus 1 are provided as one of the functions of chemical liquid injector 100, sensor head 10 fixed to the patient is preferably connected to injection head 110 placed near the patient, rather than to injection control unit 101.

Next, the operation of leak detecting sensor 1 in the present embodiment is described.

Prior to the fixing of sensor head 1 to the patient, the injection needle is inserted into a blood vessel of the patient. The injection needle is typically inserted into a blood vessel of an arm of the patient. After the insertion of the injection needle, sensor head 10 is fixed to the patient with an adhesive sheet such that the center of contact surface 17 (the center of sensor head 10) is located substantially immediately above a leading end of the inserted injection needle, and preferably, the leading end of the injection needle is located toward the front of the center of contact surface 17 (the center of sensor head 10).

Since grooves 15a are formed in the upper surface of housing 15 as described above, the intersection of grooves 15a can be located substantially immediately above the leading end of the injection needle, preferably at a position ahead of the leading end of the injection needle, to perform proper positioning of the injection needle and sensor head 10 easily. Since the injection needle is inserted along the blood vessel, housing 15 is fixed such that the longitudinal direction of one of grooves 15 formed in housing 15 coincides with the insertion direction of the injection needle, which can place light-emitting elements 11 symmetrically with respect to the blood vessel. This allows more favorable detection of an extravascular leak of the contrast medium.

Grooves 15 formed in the upper surface of housing 15 in the present embodiment function as a mark representing the guide of a position and/or an orientation in fixing sensor head 10 (housing 15) to the patient. As long as the function is realized, grooves 15 may have an arbitrary shape without being limited to the cross shape. The guide provided in the upper surface of housing 15 can have an arbitrary form which can be visually recognized, and may be formed as a protruding portion or formed by printing, instead of grooves 15.

A double-sided adhesive sheet or a single-sided adhesive sheet can be used as the adhesive sheet for fixing sensor head 10 to the patient. When the double-sided adhesive sheet is used as the adhesive sheet, sensor head 10 can be fixed to the patient by putting the double-sided adhesive sheet onto the body surface of the patient and then pressing contact surface 17 of sensor head 10 onto the adhesive sheet. Alternatively, the single-sided adhesive sheet having a relatively large area can be used as the adhesive sheet. In this case, sensor head 10 can be fixed to the patient by putting sensor head 10 and the single-sided adhesive sheet onto the patient an that sensor head 10 is covered with the adhesive sheet. Alternatively, both of them can be used together.

As described above, housing 15 of sensor head 10 is formed in the domical shape. When sensor head 10 is covered with the adhesive sheet and fixed, sensor head 10 can be fixed to the patient more stably since the adhesion area of the adhesive sheet to housing 15 is larger as compared with the case where sensor head 10 has a flat upper surface.

After sensor head 10 is fixed to the patient, the operator performs a predetermined operation to start leak detecting operation by leak detecting sensor 1.

In the leak detecting operation, light-emitting elements 11 are pulsed-driven and caused to emit light. The emitted light passes through opening portion 17b and irradiates the patient. The light applied to the patient is partially reflected on the body surface and within the body of the patient. Part of the reflected light enters into housing 15 through opening portion 17a and is received by light-receiving element 12. Light-receiving element 12 outputs an electric output value (for example, a voltage value or a current value) in accordance with the intensity of the received light to leak detecting section 30.

If an extravascular leak of the chemical liquid does not occur, the output value from light-receiving element 12 is not changed. When an extravascular leak of the chemical liquid occurs, however, part of the light entering into the body of the patient is absorbed by the chemical liquid leaked to a peripheral organ outside the blood vessel. As a result, the intensity of the reflected light is lowered to reduce the intensity of the light received in light-receiving element 12. Since this changes the output value from light-receiving element 12, leak determining section 30 determines that the extravascular leak occurs when the change of the output value from light-receiving element 12 is larger than a predetermined level.

The determination result of leak determining section 30 is used similarly to the conventional case, and for example, is output to the control section of the chemical liquid injector. In response to the output from leak determining section 30, the control section of the chemical liquid injector displays the occurrence of the extravascular leak on the display device and/or stops the injection operation of the chemical liquid.

According to leak detecting sensor 1 of the present embodiment described above, since four light-emitting elements 11 are placed around one light-receiving element 12, the center of the overall irradiation range provided by combining the irradiation ranges of light from all light-emitting elements 11 substantially coincides with the center of the light reception range of light-receiving element 12. Consequently, when sensor head 10 is fixed to the patient in any orientation, the leak of the chemical liquid can be detected without dependence on the orientation of sensor head 10, thereby improving the flexibility in fixing sensor head 10 to the patient.

Since four light-emitting elements 11 are placed to surround one light-receiving element 12, four light-emitting elements 11 irradiate the patient with the light all around light-receiving element 12 on the outside thereof. Thus, even when sensor head 10 is peeled to raise part of contact surface 17 from the patient, light-receiving element 12 is hardly influenced by external light, and the stable detection result can be obtained.

When only some of light-emitting elements 11 are driven as described later, and sensor head 10 is raised at the position of light-emitting element 11 not driven, external light may be repeatedly reflected and travels between contact surface 17 and the body surface of the patient, and finally, may reach light-receiving element 12 through opening portion 17a. To prevent this, the region of contact surface 17 including at least the periphery of opening portion 17a is colored black to allow contact surface 17 to absorb the external light easily in the present embodiment. This can further reduce the influence of the external light to provide more stable detection results.

The peeling of sensor head 10 can be detected as described below, for example.

When sensor head 10 is peeled, light-receiving element 12 detects disturbance light to result in a higher intensity of received light, so that the output value is higher than that when the disturbance light is not detected. Thus, when the output value from light-receiving element 12 in the timing of detection of the light from light-emitting elements 11 is higher than the output value at the absence of an extravascular leak of the chemical liquid, light-receiving element 12 receives the light other than the light from light-emitting elements 11, that is, the disturbance light, and leak determining section 30 can determine that sensor head 10 is peeled. When light-receiving element 11 provides an output value equal to or higher than a predetermined value in the timing other than the detection of the light from light-emitting elements 11, the light is received in the state in which light-receiving element 11 should not receive light, so that leak determining section 30 can also determine that sensor head 10 is peeled.

Four light-emitting elements 11 may be driven simultaneously or may be driven in different light-emission timings, or may be driven in combination thereof to alternate the simultaneous driving of all light-emitting elements 11 and the driving in different light-emission timings. With the simultaneous driving of all light-emitting elements 11, a large amount of light can be provided to detect a leak at a site deep below the body surface. On the other hand, when light-emitting elements 11 are driven in different light-emission timings, the number of light-emitting elements 11 to be driven and the order of the driving are arbitrarily set as long as all light-emitting elements 11 are driven uniformly. For example, light-emitting elements 11 can be driven one by one in predetermined timings clockwise or counterclockwise. Alternatively, all light-emitting elements 11 are divided into two groups each consisting of opposite pairs, and the groups can be alternately driven in predetermined and different light-emission timings. The light-emitting element 11 to be driven and the driving timing of light-emitting element 11 are controlled by sensor control section 20. When light-emitting elements 11 are driven in different light-emission timings in this manner such that only some of them emit light at a time, a site of a leak of the chemical liquid, when detected, can be roughly predicted on the basis of light-emitting element 11 driven in the timing in which the leak is detected.

In leak detecting sensor 1 of the present embodiment, light-transmitting member 18 is fitted in each of opening portions 17a and 17b formed in housing 15 for passing the light therethrough to provide contact surface 17 as the flat surface with no concaves or convexes. As a result, a foreign matter or the chemical liquid does not tend to stay on contact surface 17, which can prevent a reduction in detection sensitivity due to the foreign matter or the chemical liquid. Even when any foreign matter or the chemical liquid adheres to contact surface 17, they can be removed extremely easily since contact surface 17 is flat.

Figure 9:
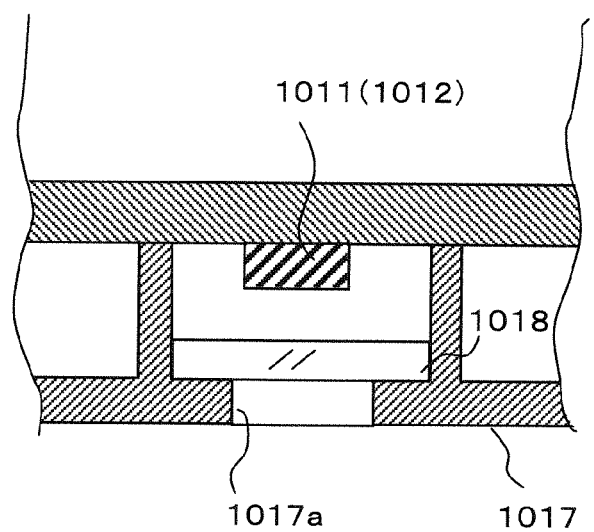
FIG. 9 A longitudinal section view showing the structure of an example of a conventional sensor head near an opening portion.

As shown in FIG. 9, light-transmitting member 1018 of a flat plate shape is held to close opening portion 1017a from inside a housing in a typical conventional sensor head. Even when contact surface 1017 is brought into intimate contact with a patient, an air layer which prevents intimate contact with the patient is formed between the body surface of the patient and light-transmitting member 1018 at opening portion 1017a. Light emitted to the patient by light-emitting element 1011 and light reflected within the body of the patient and incident on light-receiving element 1012 pass through the air layer. Since the air layer acts as various lenses since the air layer varies in thickness or shape of an interface to the body surface of the patient due to different forces for pressing the sensor head against the patient or different elasticity levels of the body of the patient, the air layer is a cause of unstable detection results.

In contrast, in sensor head 10 of the present embodiment, light-transmitting member 18 is fitted in each of opening portions 17a and 17b, so that light-transmitting member 18 is in intimate contact with the patient in the areas in which opening portions 17a and 17b are formed. The light emitted by light-emitting element 11 does not pass through the air layer as conventional methods but is reflected within the body of the patient and incident on light-receiving element 12. Thus, since light-transmitting member 18 is in intimate contact with the patient in the sites in which opening portions 17a and 17b are formed, a certain intimate contact state can be achieved between contact surface 17 and the patient. This can provide stable detection results which do not depend on the pressing force of sensor head 10 to the patient or the elasticity of the body of the patient.

Since the output value from light-receiving element 12 varies among patients, calibration is typically performed with no injection of the chemical liquid prior to the leak detection, and the output value obtained in the calibration is used as a reference value.

While the present invention has been described with the representative embodiment, the present invention is not limited to the embodiment described above, and can be changed arbitrarily without departing from the scope of technical idea of the present invention.

For example, the above embodiment has been described in the case where the number of light-emitting elements 11 is four. However, the number may be two, three, or five or more as long as light-emitting elements 11 are placed to surround light-receiving element 12. Even when the number of light-emitting elements 11 is other than four, the driving of light-emitting elements 11 can be performed as described above such that light-emitting elements 11 are driven one by one in different light-emission timings, or light-emitting elements 11 are divided into a plurality of groups each consisting of a plurality of light-emitting elements 11 and the respective groups are driven in different light-emission timings. Typically, as the number of light-emitting elements 11 is smaller, the effect of eliminating the dependence on the orientation of sensor head 10 and the stable detection performance as described above tend to reduce. As the number of light-emitting elements 11 is larger, sensor head 10 is complicated in structure and increased in size. Thus, the number of light-emitting elements 11 is determined in view of the balance between them, and specifically, the number from four to six is preferable.

Figure 10:
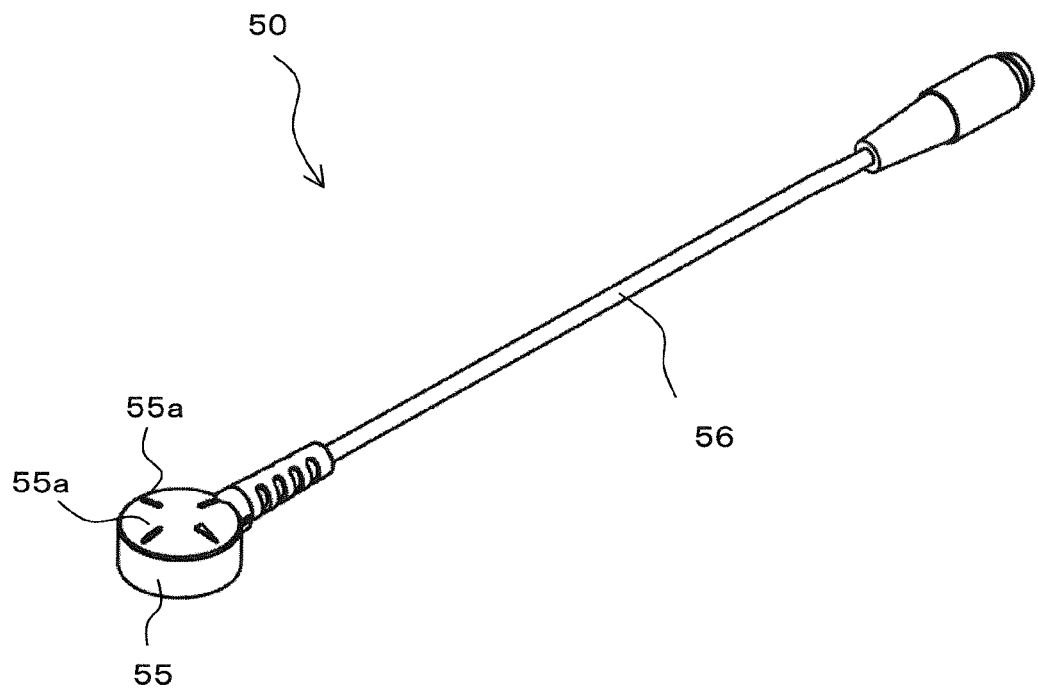
FIG. 10 A perspective view of a sensor head according to another embodiment of the present invention viewed from above.
Figure 11:
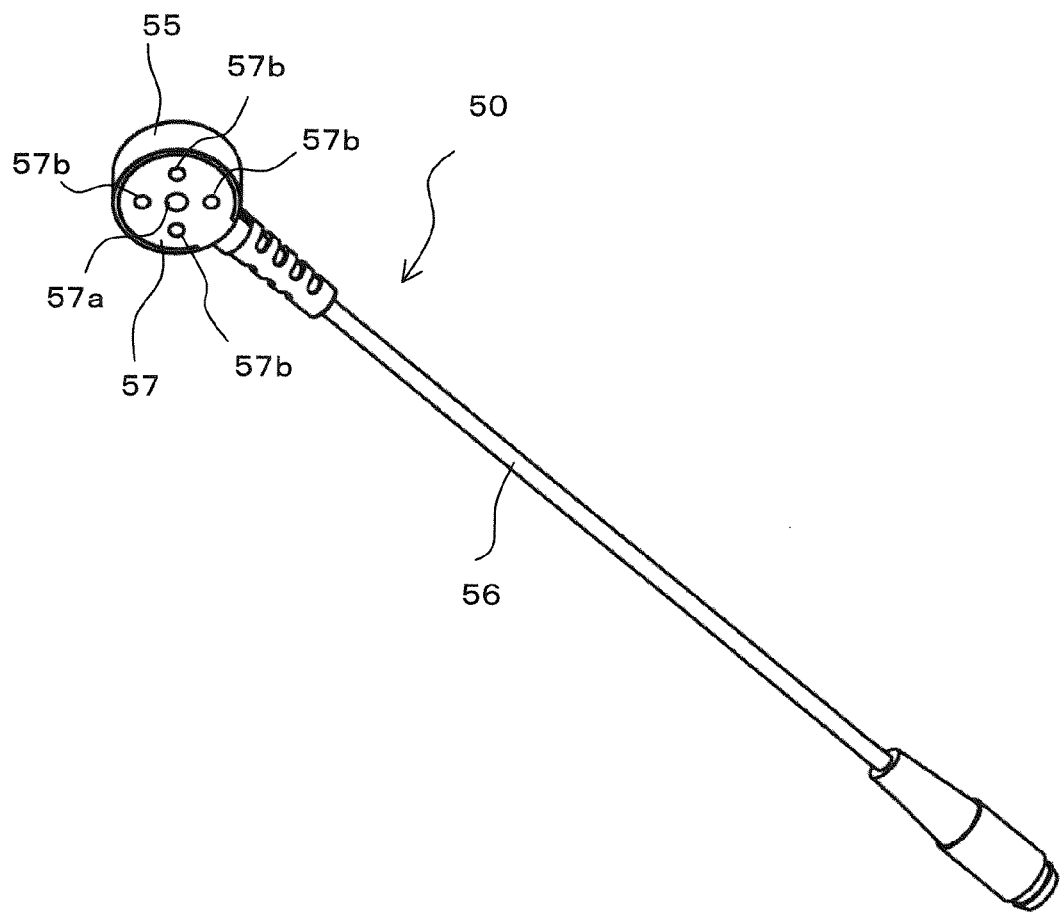
FIG. 11 A perspective view of the sensor head shown in FIG. 10 viewed from a contact surface in intimate contact with a patient.
Figure 12:
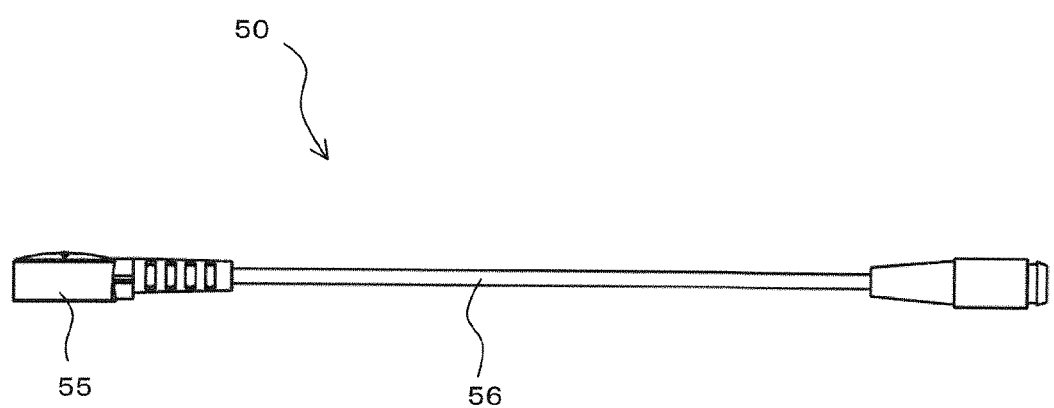
FIG. 12 A side view of the sensor head shown in FIG. 10.

While the above embodiment has shown sensor head 10 including housing 15 formed in the domical shape, the housing may have an arbitrary shape as long as the surface in contact with the patient is flat. For example, as shown in FIG. 10 to FIG. 12, sensor head 50 can have housing 55 having a flat cylindrical shape including one end surface as contact surface 57. A plurality of light-emitting elements (not shown) and one light-receiving element (not shown) are placed within housing 55 similarly to the embodiment described above.

One opening portion 57a associated with the light-receiving element and a plurality of opening portions 57b associated with the light-emitting elements are formed in contact surface 57 to be attached to the patient. A plurality of protruding portions 55a of a cross shape are formed in an upper surface of housing 55 for use in positioning of sensor head 50 and an injection needle in fixing sensor head 50 to the patient. The light-emitting elements and the light-receiving element placed within housing 55 can be connected to the chemical liquid injector through cable 56.

DESCRIPTION OF REFERENCE NUMERALS

1 LEAK DETECTING SENSOR
10, 50 SENSOR HEAD
11 LIGHT-EMITTING ELEMENT
19 HOLD MEMBER
12 LIGHT-RECEIVING ELEMENT
13 SUBSTRATE
15, 55 HOUSING
16, 56 CABLE
17, 57 CONTACT SURFACE
18 LIGHT-TRANSMITTING MEMBER
17a, 17b, 57a, 57b OPENING PORTION
20 SENSOR CONTROL SECTION
30 LEAK DETERMINING SECTION
100 CHEMICAL LIQUID INJECTOR
101 INJECTION CONTROL UNIT
110 INJECTION HEAD
200C, 200P SYRINGE

The invention claimed is:

1. A leak detecting sensor adapted to detect a leak of a chemical liquid, which should be injected into a blood vessel of a patient, to the outside of the blood vessel, the leak detecting sensor comprising:
a plurality of light sources, each emitting light to be applied to the patient; and
a single light sensor receiving the light emitted by the plurality of light sources and reflected by the patient,
a housing having a contact surface which contacts a body surface of the patient, wherein the housing contains the light sources and the light sensor such that the light emitted from each of the light sources is emitted to an outside of the housing through the contact surface and the light sensor receives the light which enters into the housing through the contact surface,
a sensor control circuit configured to control which light source is driven in which timing in accordance with a preset procedure, and
a voltage or current detector configured to determine a leak of the chemical liquid and output an electrical leak detection signal when the voltage or current detector determines that the leak has occurred,
wherein the plurality of light sources are placed to surround the single light sensor,
the sensor control circuit drives the light sources in a pulse drive, such that the light sources emit the light in a pulsed pattern; and
wherein the voltage or current detector is configured to determine the leak of the chemical liquid when a reduction of the electrical output value from the light sensor is larger than a predetermined level and determine a peeling of the housing when the light sensor provides the electrical output value equal to or higher than a predetermined value in a timing other than the detection of the light from the light sources.

2. The leak detecting sensor according to claim 1, further comprising a housing holding the light sources and the light sensor,
wherein the housing has a plurality of opening portions formed therein for passing the light, the opening portions being formed at positions opposite to the light sources and the light sensor.

3. The leak detecting sensor according to claim 1, wherein the opening portion opposite to the light sensor is formed at the center of the contact surface.

4. The leak detecting sensor according to claim 1, wherein an upper surface of the housing is formed in a domical shape, the upper surface being opposite to the contact surface.

5. The leak detecting sensor according to claim 1, wherein the housing has a flat cylindrical shape having one end surface as the contact surface.

6. The leak detecting sensor according to claim 1, wherein a light-transmitting member transmitting the light emitted by the light-emitting element is fitted in the opening portion, and thus the contact surface is flat including a lower surface of the light-transmitting member.

7. The leak detecting sensor according to claim 1, wherein the voltage or current detector determines that the housing is peeled, when the output value from the light sensor is higher than a predetermined value.

8. The leak detecting sensor according to claim 1, wherein the sensor control circuit is configured to drive the light sources such that the light sources are divided into groups each consisting of opposite pairs and the groups are alternately driven in different light emission timings.

9. The leak detecting sensor according to claim 1, wherein the sensor control circuit is configured to drive the light sources such that the light sources are driven simultaneously.

10. The leak detecting sensor according to claim 1, wherein the sensor control circuit is configured to drive the light sources such that the light sources are driven in different light emission timings.

11. A liquid injection system comprising:
the leak detecting sensor according to claim 1; and
a chemical liquid injector injecting a chemical liquid of interest in detection of a leak by the leak detecting sensor,
wherein the chemical liquid injector controls operation of injection of the chemical liquid and operation of the leak detecting sensor.

* * * * *